(12) United States Patent
Melnyk

(10) Patent No.: US 6,237,429 B1
(45) Date of Patent: May 29, 2001

(54) SOIL SAMPLING APPARATUS

(75) Inventor: John P. Melnyk, Calgary (CA)

(73) Assignee: BR Tools Inc., Calgary (CA)

( * ) Notice: Subject to any disclaimer, the term of this patent is extended or adjusted under 35 U.S.C. 154(b) by 0 days.

(21) Appl. No.: 09/385,640

(22) Filed: Aug. 27, 1999

(30) Foreign Application Priority Data

Oct. 20, 1998 (CA) .................................................. 2251644

(51) Int. Cl.$^7$ ....................................................... G01N 1/08
(52) U.S. Cl. ....................................................... 73/864.45
(58) Field of Search ........................... 73/864.44, 864.45, 73/864.74; 175/20, 28

(56) References Cited

U.S. PATENT DOCUMENTS

| | | | |
|---|---|---|---|
| 3,666,028 | * | 5/1972 | Greene . |
| 4,336,849 | * | 6/1982 | Hug . |
| 4,989,678 | * | 2/1991 | Thompson . |
| 5,070,372 | * | 12/1991 | Hellbusch . |
| 5,211,248 | * | 5/1993 | Nosewicz . |

* cited by examiner

Primary Examiner—Robert Raevis
(74) Attorney, Agent, or Firm—George A. Seaby

(57) ABSTRACT

A relatively simple soil sampler includes a carrier for mounting on a vehicle, a mast, a carriage slidable on the mast carrying a hammer and in the form of a flighted auger of sample extraction a core tube beneath the hammer, whereby, when the carriage is moved downwardly to a position in which the core tube engages the ground, continued downward movement of the carriage brings the hammer into engagement with the core tube to drive the core tube into the ground, a winch on the mast connected to the top end of the carriage by a cable for moving the carriage upwardly to retract the core tube from the ground.

9 Claims, 5 Drawing Sheets

SOIL SAMPLING APPARATUS

BACKGROUND OF THE INVENTION

1. Field of the Invention

This invention relates to a soil sampler.

While the invention is referred to as a soft soil sampler, it will be appreciated that the device can be used to obtain samples of hard, compacted or frozen ground such as permafrost, or samples of a variety of other materials such as peat, muskeg and shale. Accordingly, the term "soil", as used herein, should be given a broad interpretation.

2. Discussion of the Prior Art

Soil or core samplers are by no means new. Examples of such devices are disclosed by U.S. Pat. No. 2,701,121 issued to A. D. Bull on Feb. 1, 1955; U.S. Pat. No. 2,709,368, issued to D. E. Wolpert on May 1, 1955; U.S. Pat. No. 2,868,019, issued to A. D. Bull on Jan. 13, 1959; U.S. Pat. No. 3,817,334, issued to Henry Bolt on Jun. 18, 1974; U.S. Pat. No. 4,191,263, issued to T. J. Malterer on Mar. 4, 1980; U.S. Pat. No. 4,316,393, issued to H. Philipenko on Feb. 23, 1982; U.S. Pat. No. 4,333,541, issued to J. G. Doty on Jun. 8, 1982; U.S. Pat. No. 4,482,021, issued to Roman Repski on Nov. 13, 1984; U.S. Pat. No. 5,213,169, issued to M. E. Heller on May 25, 1993; U.S. Pat. No. 5,394,949, issued to N. A. Wright et al on Mar. 7, 1995 and 5,435,399, issued to G. G. Peterson et al on Jul. 25, 1995. In general, the patented devices are somewhat complicated, and often cumbersome and consequently can be used on a truck or other large vehicle only.

Accordingly, a need still exists for a soil sampler which can be used on a variety of vehicles, including small trucks, trailers or all terrain vehicles.

GENERAL DESCRIPTION OF THE INVENTION

An object of the present invention is to meet the above defined need by providing a relatively simple, lightweight soil sampler, which can be mounted on a variety of vehicles.

Another object of the invention is to provide a soil sampler constructed of a few, structurally simple components which are easy to assemble and to operate.

Accordingly, the invention relates to a soil sampler comprising an elongated mast; a carrier for mounting the mast on a vehicle; a carriage slidable on said mast; a hammer on said carriage for movement with said carriage; a core tube slidable on said carriage beneath said hammer, whereby, when the carriage is moved downwardly to a position in which the core tube engages the ground, continued downward movement of the carriage brings the hammer into engagement with the core tube and actuation of said hammer drives the core tube into the ground; a winch on said mast; and a cable connecting said winch to a top end of said carriage for moving said carriage upwardly to draw the core tube from the ground.

BRIEF DESCRIPTION OF THE DRAWINGS

The invention is described below in greater detail with reference to the accompanying drawings which illustrate a preferred embodiment of the invention, and wherein:

FIG. 4 is an isometric view of the central area of a mast and a carrier used in the soil sampler of FIGS. 1 to 3;

FIG. 5 is an exploded, isometric view of the mast and carrier of FIG. 4;

DESCRIPTION OF THE PREFERRED EMBODIMENT

Figure 1:
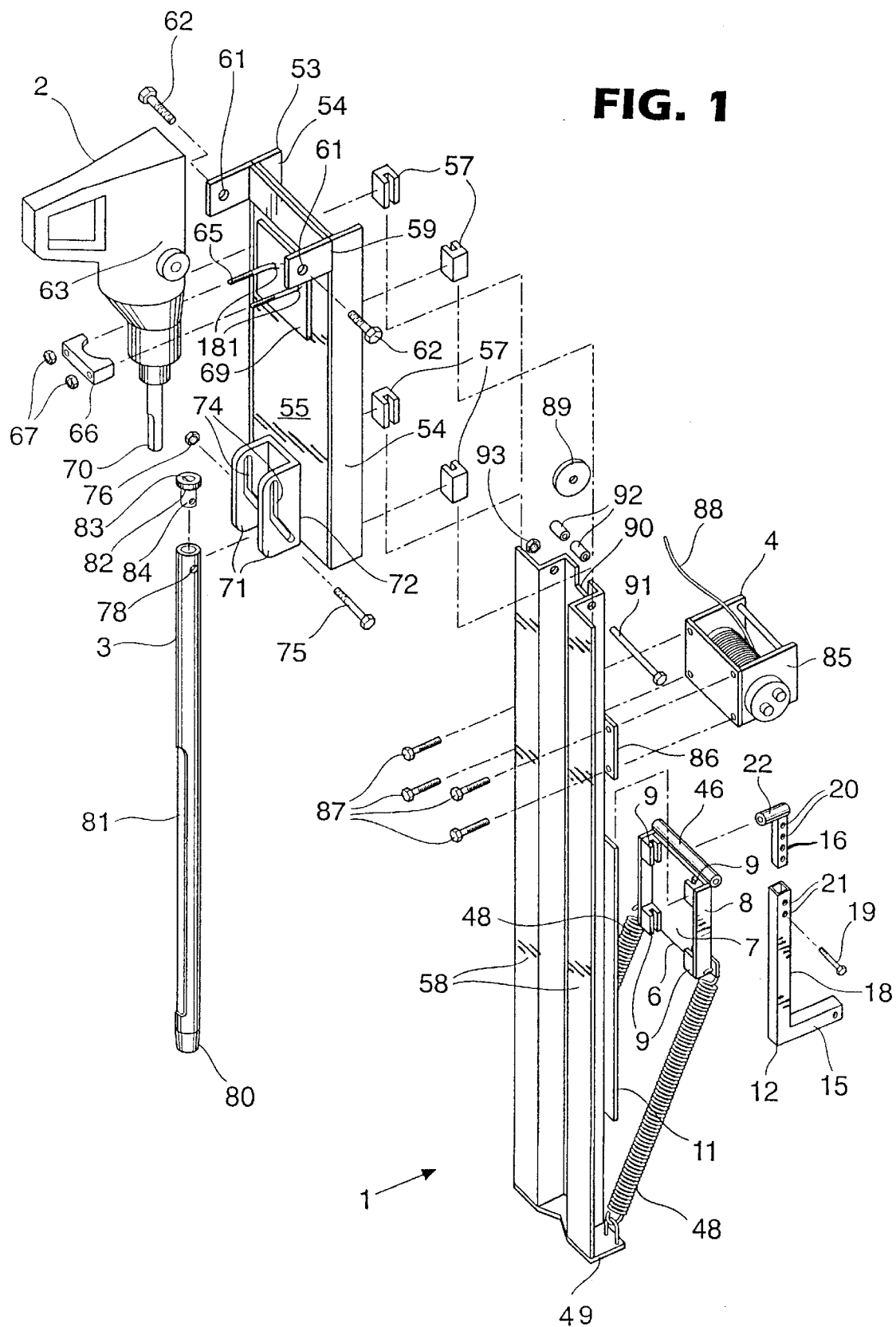
FIG. 1 is an exploded, isometric view of a soil sampler in accordance with the invention.
Figure 2:
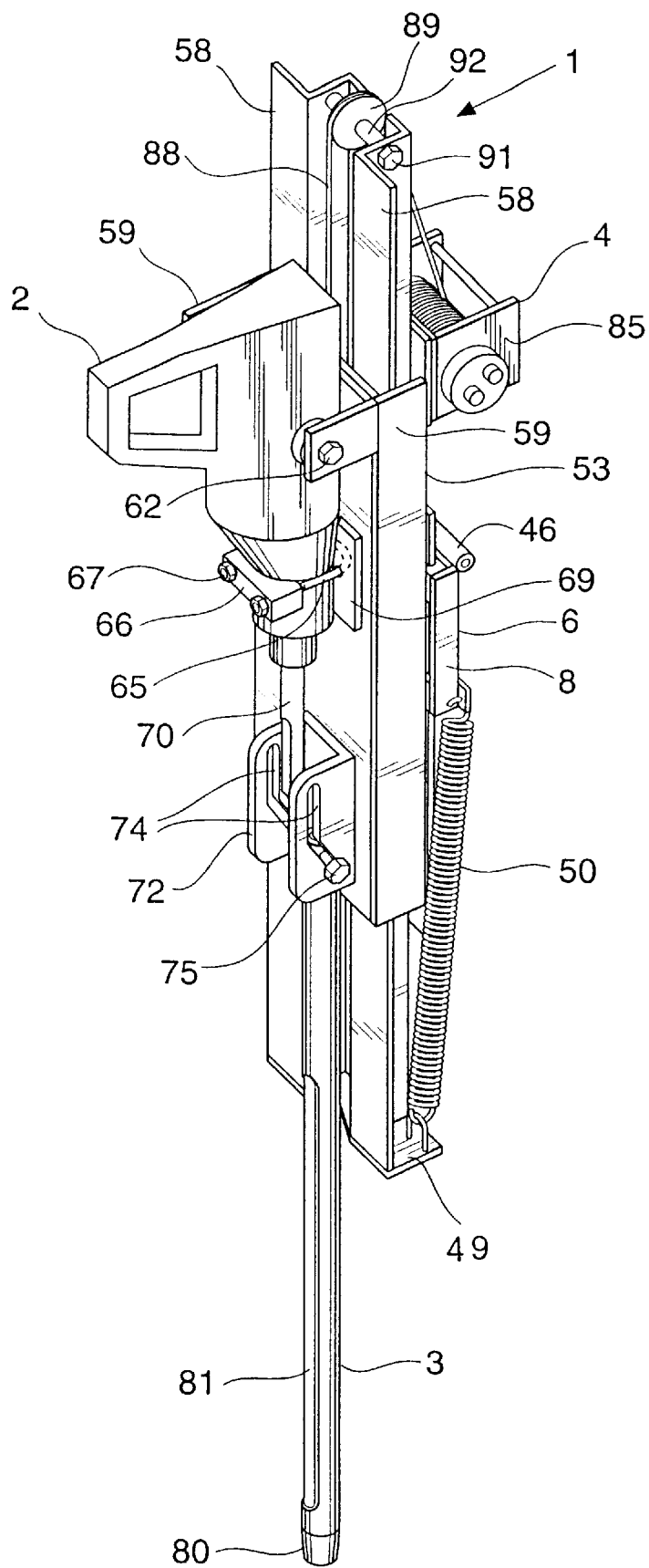
FIG. 2 is an isometric view from above and one side of the soil sampler of FIG. 1 in assembled condition.
Figure 3:
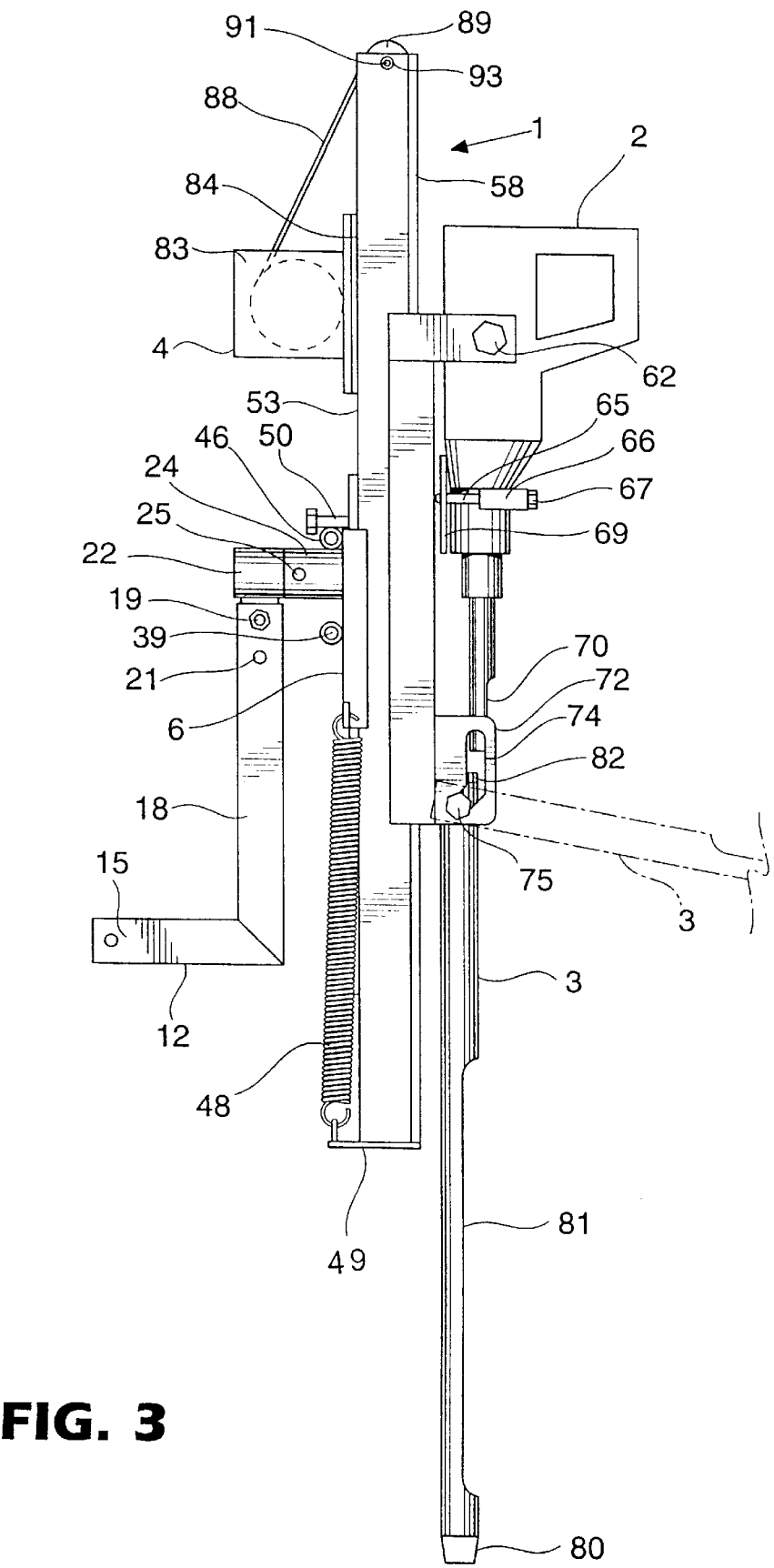
FIG. 3 is a side view of the soil sampler of FIGS. 1 and 2.
Figure 6:
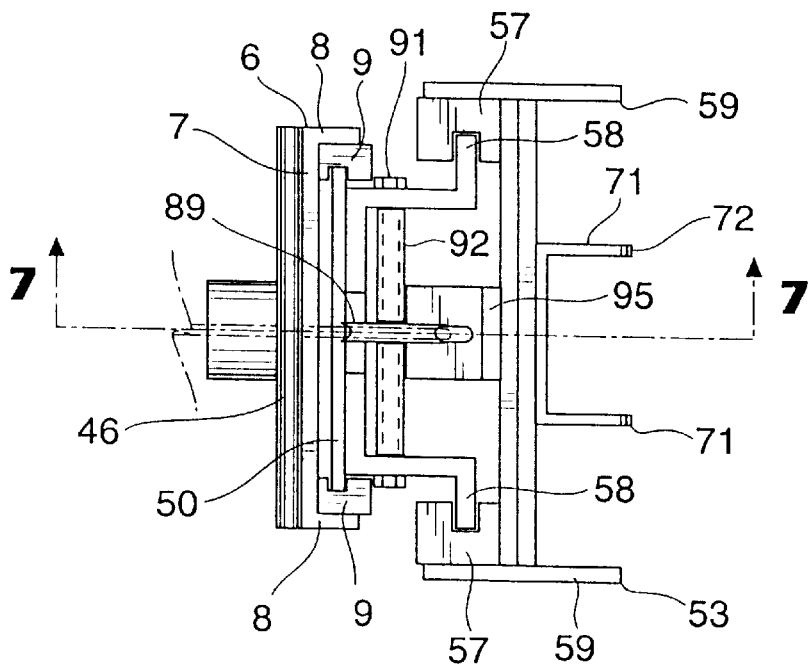
FIG. 6 is a top view of the soil sampler with parts omitted.

Referring to FIGS. 1 to 3, the basic elements of the soil sampler include a mast generally indicated at 1 carrying a rotary hammer 2, a sample extractor defined by a core tube 3 and a winch 4. The sample extractor can also be a flighted auger (not shown) which is simultaneously rotated and hammered permitting penetration to a greater depth. The mast 1 is slidably mounted in a carrier 6 defined by an outer plate 7 and side plates 8 with longitudinally grooved blocks 9 mounted on the top and bottom of the inner surface of each side plate 8. The grooves in the blocks 9, oppose each other defining tracks for receiving the sides or wings of a rectangular plate 11 on the mast 1, whereby the mast 1 can slide in the carrier 6. The carrier 6 is mounted on the front or rear end of a truck or other vehicle (not shown) using an L-shaped post 12 (FIGS. 1 and 3) or on the rear of an all terrain vehicle (not shown) using a skeletal frame 13 (FIGS. 4 and 5).

When the carrier 6 is mounted on one end of a vehicle, the tubular, bottom horizontal arm 15 of the post 12 is connected to a hitch bar (not shown) on the vehicle. A bar 16 is slidably mounted in the square cross section, tubular, vertical arm 18 of the post 12. The bar 16 is fixed in one position by a bolt 19, which is inserted into aligned holes 20 and 21 in the bar 16 and the arm 18, respectively. By providing a plurality of holes 20 and 21, the height of the carrier 6 can readily be adjusted. A horizontal arm 22, (FIG. 1) on the top end of the bar 16 is inserted into a socket 24 (FIG. 3) extending outwardly from the plate 7. The arm 22 is locked in the socket 24 by a pin 25.

Figures 4, 5:
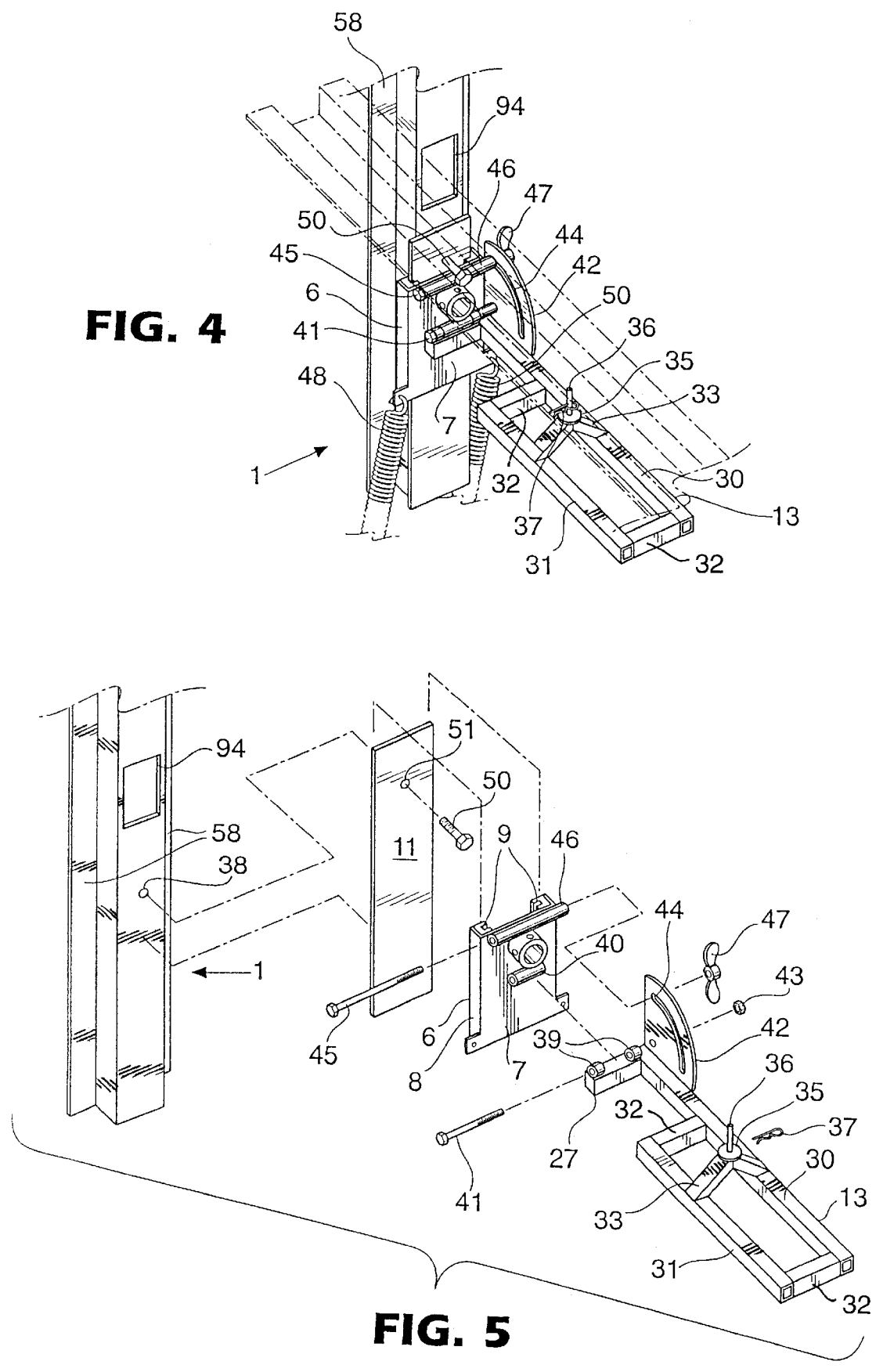

Alternatively, as best shown in FIGS. 4 and 5, the carrier 6 is pivotally mounted on an arm 27 on the outer end of the skeletal frame 13 extending transversely of the top, rear end of an all terrain vehicle (not shown). The frame 13 permits movement of the mast, from a storage or transport position (shown in phantom outline in FIG. 4) to a vertical, use position (shown in solid outline in FIGS. 3 and 4).

The frame 13 includes a long side 30 carrying the arm 27, a short side 31 and crossbars 32 extending between the sides 30 and 31. An inverted V-shaped stand 33 extends between the sides 30 and 31 for supporting the mast 1 in the transport or non-use position. When in the storage position, the mast 1 rests on a circular plate 35 on the top end of the stand 33. A post 36 on the plate 35 extends through a hole 38 (FIG. 5) in the mast 1, and a pin 37 is used to releasably secure the masts 1 on the stand 33.

The sampler is connected to the frame 13 (which is fixedly mounted on the all terrain vehicle) by a pair of sleeves 39 on the arm 27 of the frame 13 which are aligned with a sleeve 40 on the plate 7. A bolt 41 extends through the sleeves 39 and 40, and the 90° corner of a wedge-shaped plate 42 on the long side 30 of the frame 13 to pivotally connect the carrier 6 to the frame 13 and consequently to the all terrain vehicle. A nut 43 on the bolt 41 holds the assembly together. The wedge-shaped plate 42 has an arcuate slot 44 for receiving a bolt 45. The bolt 45 extends through a sleeve 46 on the top end of the carrier 6. A wing nut 47 is used to lock the carrier 6 in position, i.e. the use or non-use position. The wing nut 47 is loosened to permit rotation of the carrier 6 and consequently the mast 1 around the longitudinal axis of the bolt 41. When the mast 1 is in the desired position, the wing nut 47 is tightened to lock the mast 1 in position. While the frame 13 was designed for use on an all terrain vehicle, it will be appreciated that the frame 13 can be mounted on the bed of a truck or other vehicle, with the frame 13 extending longitudinally of the vehicle.

When vertically oriented, the mast 1 is biased to an elevated position by a pair of helical springs 48 extending from the bottom of the carrier 6 to a baseplate 49 on the bottom of the mast 1. Thus, with the mast 1 in the vertical position, the sampler can be moved short distances without damaging the mast 1 or the remainder of the sampler. When the sampler is to be transported over a long distance, a bolt 50 (FIGS. 3 to 5) is inserted into aligned holes 51 and 38 (FIG. 5) in the plate 11 and the mast 1. The bolt 50 is held in position by the pin 37, which is inserted into a diametrically extending hole (not shown) in the inner end of the bolt on the inside of the mast 1. The bolt 50 limits downward movement of the mast 1 and the plate 11 in the carrier 6. Alternatively, the mast 1 is removed from the end of the vehicle (FIG. 3) or rotated to the transport position on the frame 13 (FIG. 4).

The rotary hammer (which is available from Hitachi) is mounted on the top end of a carriage 53, which is slidable on the mast 1. Like the carrier 6, the carriage 53 is generally U-shaped in cross section, including a pair of sides 54 interconnected by a rectangular plate 55. Four notched blocks 57 are mounted at the top and bottom corners of the plate 55. The notches in the blocks 57 are opposed for sliding on tracks defined by wings 58 on the mast 1. The arms of a generally U-shaped bracket 59 extend outwardly from the top end of the carriage 53 for supporting the hammer 2. Holes 61 (FIG. 1) in the bracket 59 receive bolts 62, which extend into threaded sockets 63 (one shown) on the hammer 2. A U-bolt 65 welded to the plate 55, a yoke 66 and nuts 67 secure the bottom end of the hammer 2 the carriage 53. A rubber pad 69 mounted on the U-bolt 65 protects the rotary hammer 2.

The shaft 70 of the hammer 2 extends downwardly between the sides 71 of a bracket 72 on the bottom end of the carriage 53. Generally chevron-shaped slots 74 are provided in the sides 71 of the bracket 72 for slidably receiving a bolt 75. The bolt 75 is retained in the slots 74 by a nut 76. The bolt 75 extends through diametrically opposed holes 78 (one shown—FIG. 1) in the top end of the core tube 3 for retaining such top end between the sides 71 of the bracket 72. The core tube 3 is open at both ends with a tapered bottom end 80 facilitating the hammering of the tube into the ground. A slot 81 extends longitudinally of the outer side of the tube 3 permitting removal of a core sample from the tube. A cap 82 is mounted on the top end of the tube 3. The cap transmits the force of impact of the hammer 2 to the tube 3. A recess or socket 83 in the head of the cap 82 receives the bottom, free end of the shaft 70. The socket 83 ensures that the force of the hammer 2 is applied evenly to the top end of the core tube 3. The cap 82 is retained on the top end of the core tube 3 by the bolt 75 which extends through the holes 78 and an aligned, diametrically extending hole 84 (FIG. 2) in the cap 82.

Figure 7:
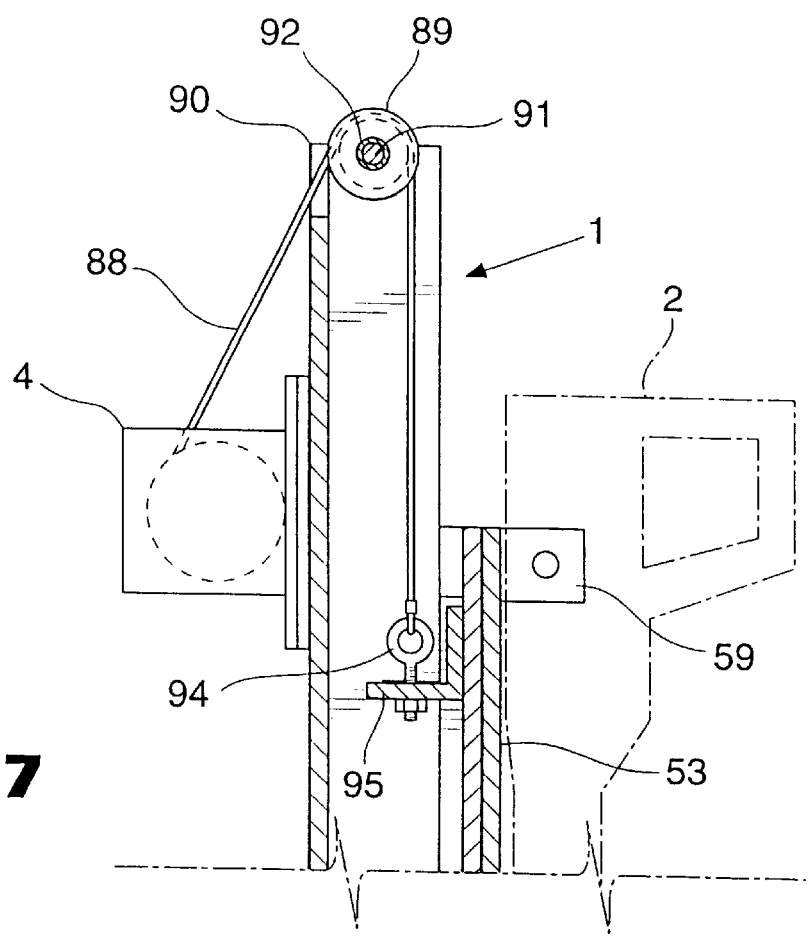
FIG. 7 is a cross section of the top end of the soil sampler taken generally along line 7—7 of FIG. 6 with parts omitted.

The carriage 53 and consequently the hammer 2 and the core tube 3 are moved upwardly using the winch 4. The winch 4 includes a frame 85 mounted on a plate 86, which is secured to the side of the mast 1 opposite the carriage 53 and the hammer 2. The frame 85 is connected to the mast 1 by bolts 87. The winch cable 88 extends upwardly around a pulley 89 mounted in a notch 90 in the top end of the mast 1. The pulley 89 is rotatably mounted on a bolt 91 extending through the sides of the mast 1 The pulley 89 is centered between the sides of the mast 1 by sleeves 92 on the bolt 91, and held in position by a nut 93. As best shown in FIG. 7, the outer end of the cable 88 is secured to an eyebolt 94 mounted in an angle iron bracket 95 on the inner surface of the plate 55 of the carriage 53. An opening 97 (FIGS. 4 and 5) in the mast 1 provides for access to the outer end of the cable 88 and the eyebolt 94. Although the cable 88 is fixed to the eyebolt 94, it will be appreciated that the cable 88 may pass through a pulley (not shown) attached to eyebolt 94, extended to the top of the mast 2 and fixed on the bolt 90. This halves the work load of the winch.

As a preliminary to taking a core sample, the sampler is mounted on a trailer hitch or pivoted from the transport to the vertical use position. When not in use, the shaft 70 of the rotary hammer 2 is not in contact with the core tube 3 (FIGS. 2 and 3). In operation, the winch cable 88 is released and the carriage 53, to which the hammer 2 and tube 3 are attached, is moved downwardly. The bottom end of tube 3 engages the ground and the top end of tube 3 is moved outwardly and upwardly by sliding the bolt 75 up the inclined bottom end of the slot 74. The bottom end of the shaft 70 is inserted into the top end of the pounding cap 2 of the core tube 3. The hammer 2 is actuated to drive the tube 3 downwardly. Thus, the force of the hammer impact is applied evenly to the top of the tube 3. Continued operation of the hammer 2 drives the core tube 3 into the ground.

After the tube 3 has been driven a sufficient distance into the ground, i.e. the slot 81 is no longer visible above the ground, the hammer 2 is stopped and the winch 4 is actuated. The winch 4 draws the mast 1 downwardly, stretching the springs 48 until the base plate 49 engages the ground. After the base plate 49 engages the ground winch 4 can draw the carriage 53 upwardly. Consequently, the tube 3 is pulled out of the ground. As the tube 3 clears the surface of the ground the springs 48 contact, which moves the mast 1 upwardly into a travel position. The opposing force of tube 3 in the ground moves the mast 1 downwardly into contact with the ground. Once in contact with the ground, the tube 3 is extracted from the material being sampled. Once the force of the springs 48 is greater than the skin friction force on the tube 3, the mast 1 returns to a normal vertical position.

During extraction of the tube 3 from the ground, it is preferable to reduce the moment force about the carriage cable attachment by moving the pull point of the tube 3, i.e. the bolt 75 closer to the pull point of the cable 88, i.e. the angle iron bracket 95. Because the bottom end of the slots 74 are inclined, as the carriage moves upwardly the bolt 75, in effect, slides downwardly and inwardly to the bottom of the slots 74. As shown in phantom outline in FIG. 3, once clear of the ground and the mast 1 has returned to a travel position, the core tube 3 can be swung outwardly to facilitate examination, description, sampling, and removal; of a core through the slot 81.

I claim:

1. A soil sampler comprising an elongated mast; a carrier for mounting the mast on a vehicle; a carriage slidable on said mast; a hammer on said carriage for movement with said carriage; a sample extractor slidable on said carriage beneath said hammer, whereby, when the carriage is moved downwardly to a position in which the sample extractor engages the ground, continued downward movement of the carriage brings the hammer into engagement with the sample extractor and actuation of said hammer drives the sample extractor into the ground; a winch on said mast; and a cable connecting said winch to a top end of said carriage for moving said carriage upwardly to draw the sample extractor from the ground.

2. The soil sampler of claim 1, including at least one spring connecting said carrier to said mast for biasing said mast to an elevated position above the ground, whereby the sampler can be moved short distances while the mast is vertically oriented, and said mast can move into contact with material to be sampled.

3. The soil sampler of claim 2, wherein said carrier includes a plate; a socket on said plate for mounting the plate on a vehicle hitch; first tracks on said plate; and wings on said mast slidable in said first tracks.

4. The soil sampler of claim 1, wherein said carrier includes a frame for mounting on a vehicle; a plate carrying said mast pivotally connected to said frame for rotation of the mast between a horizontal non-use position and a vertical, use position; first tracks on said plate; and wings on said mast slidable in said first tracks.

5. The soil sampler of claim 4, including at least one spring connecting said mast to said plate for biasing the mast to an elevated position above the ground, whereby the sampler can be moved short distances with the mast vertically oriented.

6. The soil sampler of claim 1, including a bracket on said carriage slidably and pivotally supporting said sample extractor for movement between hammer engaging and sample removing positions.

7. The soil sampler of claim 6, wherein said bracket includes parallel slots inclined with respect to said mast; and a bolt extending through said slots and the top end of said sample extractor, whereby the sample extractor can be moved between a ground penetrating position remote from the mast and a retraction position closer to the mast, whereby the center of gravity of the sampler is changed from the penetrating to the retraction positions.

8. The soil sampler of claim 1, wherein said carrier and winch are mounted on one side of the mast, and said carriage and sample extractor are mounted on the other side of the mast.

9. The soil sampler of claim 8, including a pulley on top of said mast for slidably supporting said cable between said carriage and said winch.

* * * * *